United States Patent
Saudan et al.

(10) Patent No.: US 7,763,758 B2
(45) Date of Patent: Jul. 27, 2010

(54) HYDROGENATION OF ESTERS WITH RU/BIDENTATE LIGANDS COMPLEXES

(75) Inventors: Lionel Saudan, Geneva (CH); Philippe Dupau, Bellegarde/Valserine (FR); Jean-Jacques Riedhauser, Dardagny (CH); Patrick Wyss, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 11/854,106

(22) Filed: Sep. 12, 2007

(65) Prior Publication Data

US 2008/0071121 A1    Mar. 20, 2008

Related U.S. Application Data

(63) Continuation of application No. PCT/IB2006/051027, filed on Apr. 4, 2006.

(30) Foreign Application Priority Data

Apr. 5, 2005    (WO) .................. PCT/IB2005/000938

(51) Int. Cl.
*C07C 29/149*    (2006.01)
(52) U.S. Cl. ...................................... 568/814; 564/489
(58) Field of Classification Search .................. 568/814, 568/885; 564/489
See application file for complete search history.

(56) References Cited

U.S. PATENT DOCUMENTS

| 2004/0015017 A1 | 1/2004 | Rautenstrauch et al. ..... 564/490 |
| 2004/0063966 A1 | 4/2004 | Rautenstrauch et al. ..... 548/400 |

FOREIGN PATENT DOCUMENTS

| GB | 2 031 883 A | 4/1980 |
| WO | WO 02/22526 A2 | 3/2002 |
| WO | WO 02/40155 A1 | 5/2002 |

OTHER PUBLICATIONS

Kerkadze, USSR Genetika, 1968, 4(2), pp. 33-40 (abstract only).*
International Search Report and Written Opinion of the International Searching Authority dated Aug. 9, 2006 from application No. PCT/IB2006/051028.
Gao et al., "New Chiral Catalysts for Reduction of Ketones," Chirality 12: 383-388 (2000).

* cited by examiner

*Primary Examiner*—Elvis O Price
(74) *Attorney, Agent, or Firm*—Winston & Strawn LLP

(57) ABSTRACT

The present invention relates to the field of catalytic hydrogenation and, more particularly, to the use of Ru complexes with bidentate ligands, having one amino or imino coordinating group and one phosphino coordinating group, in hydrogenation processes for the reduction of esters or lactones into the corresponding alcohol or diol respectively.

20 Claims, No Drawings

HYDROGENATION OF ESTERS WITH RU/BIDENTATE LIGANDS COMPLEXES

CROSS-REFERENCE TO RELATED APPLICATION(S)

This application is a continuation of International application PCT/IB2006/051027 filed on Apr. 4, 2006, the entire content of which is expressly incorporated herein by reference thereto.

TECHNICAL FIELD

The present invention relates to the field of catalytic hydrogenation and, more particularly, to the use of Ru complexes with bidentate ligands, in hydrogenation processes for the reduction of esters or lactones into the corresponding alcohol or diol respectively.

BACKGROUND

Reduction of an ester functional group to the corresponding alcohol is one of the fundamental reactions in organic chemistry, and is used in a large number of chemical processes. In general, two main types of processes are known to achieve such a transformation. Such types of processes are the following:

a) hydride processes, in which a silyl or metal hydride salt, such as $LiAlH_4$, is used;

b) hydrogenation processes, in which molecular hydrogen is used.

From a practical point of view, hydrogenation processes are more attractive as they can be run using small amounts of catalyst (typically 10 to 1000 ppm relative to the substrate) and in the presence of small quantities or even in the absence of solvent. Furthermore, hydrogenation processes do not require the use of highly reactive and expensive hydrides, and do not produce important amounts of aqueous waste.

One of the mandatory and characterizing elements of hydrogenation processes is the catalyst or the catalytic system which is used to activate the molecular hydrogen in view of the reduction. The development of useful catalysts or catalytic systems for the hydrogenation of an ester functional group represents still an important need in chemistry.

Amongst the few catalysts or catalytic systems known to perform such reductions one may cite the ruthenium/phosphine complexes, obtained by the reaction of ruthenium oxide or carboxylate precursor with a mono-, di- or tri-phosphine ligand (an example of which is described by Elsevier et al. in Chem.Commun., 1998, 1367). In this type of complex the ruthenium metal is coordinated only by "acac" ligands and phosphine atoms, limiting thus the diversity of the ligand structure and coordination sphere around the metal center. As a consequence of such little diversity the tuning of the activity and of the performance of the hydrogenation process is not easy. Furthermore, the experimental conditions require very high pressures (at least 70-130 bars) and temperatures (120-180° C.).

Therefore, there is a need for hydrogenation processes using alternative catalysts or pre-catalysts, preferably having a greater diversity in the ligand structures and coordination spheres around the metal center and allowing the use of softer experimental conditions.

SUMMARY OF THE INVENTION

The present invention now relates about a hydrogenation process for the reduction of esters, or the like, into alcohols in the presence of a base and at least one complex in the form of a ruthenium complex of a bidentate ligand wherein the coordinating groups consist of one amino or imino group and one phosphino group. The invention relates also about new ligands and complexes useful for carrying the invention process.

DETAILED DESCRIPTION OF THE PREFERRED EMBODIMENTS

In order to overcome the problems aforementioned, the present invention relates to processes for the reduction by hydrogenation, using molecular $H_2$, of a $C_3$-$C_{70}$ substrate containing one or two esters, or lactones, functional groups into the corresponding alcohol, or diol, characterized in that the process is carried out in the presence of a base and at least one catalyst or pre-catalyst in the form of a ruthenium complex of a bidentate ligand wherein the coordinating groups consist of one amino or imino group and one phosphino group.

According to an embodiment of the invention, the amino group is a primary (i.e. $NH_2$) or a secondary (i.e. NH) amino group.

According to a particular embodiment of the invention, the substrate can be a compound of formula (I)

(I)

wherein $R^a$ and $R^b$ represent, simultaneously or independently, a linear, branched or cyclic $C_1$-$C_{30}$ aromatic, alkyl or alkenyl group, optionally substituted; or $R^a$ and $R^b$ are bonded together and form a $C_4$-$C_{20}$ saturated or unsaturated group, optionally substituted.

The corresponding alcohols (i.e., (II-a) and (II-b)), or the corresponding diol (II'), of the substrate (I), are of formula

(II-a)

(II-b)

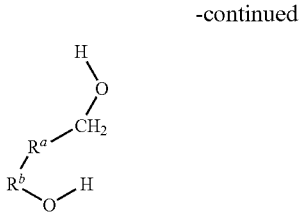

wherein $R^a$ and $R^b$ are defined as in formula (I).

A compound of formula (II) (i.e. II-a or I-b) will be obtained in the case where $R^a$ and $R^b$ are not bonded together, while a compound of formula (II') will be obtained in the case where $R^a$ and $R^b$ are bonded together.

It is understood that by "a linear, branched or cyclic . . . aromatic, alkyl, or alkenyl group" it is meant that the $R^a$ or $R^b$ can be in the form of, e.g., a linear alkyl group or can also be in the form of a mixture of the type of groups, e.g. a specific $R^a$ may comprise a linear alkyl, a branched alkenyl, a (poly) cyclic alkyl and an aryl moiety, unless a specific limitation to only one type is mentioned. Similarly, in all the below embodiments of the invention when a group is mentioned as being in the form of more than one type of topology (e.g. linear, cyclic or branched) and/or unsaturation (e.g. alkyl, aromatic or alkenyle) it is meant also a group which may comprise moieties having any one of the topologies or unsaturations, as above explained.

A particular embodiment of the invention's process is shown in Scheme 1:

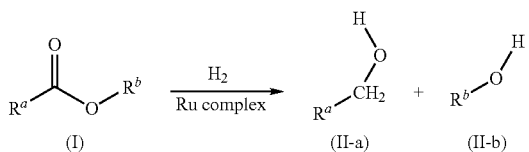

According to a further embodiment of the invention, the substrate is an ester, or lactone, that will provide an alcohol, or a diol, that is useful in the pharmaceutical, agrochemical or perfumery industry as final product or as an intermediate. Particularly preferred substrate is an ester, or lactone, that will provide an alcohol, or diol, which is useful in the perfumery industry as final product or as an intermediate.

According to another embodiment of the invention, the substrate is a $C_5$-$C_{30}$ compound of formula (I), and in particular one may cite those wherein $R^a$ and $R^b$ represent simultaneously or independently a linear, branched or cyclic $C_1$-$C_{30}$ aromatic or alkyl group optionally substituted, or a cyclic $C_5$-$C_{30}$ alkenyl group optionally substituted; or $R^a$ and $R^b$ are bonded together and form a $C_4$-$C_{20}$ saturated or unsaturated linear, branched, mono-, di- or tri-cyclic group, optionally substituted.

According to a further embodiment of the invention the substrate is a $C_5$-$C_{20}$ compound of formula (I), wherein $R^a$ and $R^b$ represent simultaneously or independently a linear, branched or cyclic $C_5$-$C_{18}$ aromatic or alkyl group, optionally substituted, or a cyclic $C_5$-$C_{18}$ alkenyl group, optionally substituted; or $R^a$ and $R^b$ are bonded together and form a $C_4$-$C_{20}$ saturated or unsaturated linear, branched, mono-, di- or tri-cyclic group, optionally substituted.

Furthermore, according to a yet further embodiment, when $R^a$ and/or $R^b$ represent an alkenyl group then the carbon-carbon double bond is not terminal and is not conjugated.

Possible substituents of $R^a$ and $R^b$ are one, two or three halogen, $OR^c$, $NR^c_2$ or $R^c$ groups, in which $R^c$ is a hydrogen atom, a halogenated $C_1$-$C_2$ group or a $C_1$ to $C_{10}$ cyclic, linear or branched alkyl, or alkenyl group, preferably a $C_1$ to $C_4$ linear or branched alkyl or alkenyl group. As other possible substituents one may also cite a group $COOR^c$, which can also be reduced to the corresponding alcohol during the invention's process, according to the molar amount of $H_2$ used, as well known by a person skilled in the art.

Non-limiting examples of substrates are alkyl cinnamates, sorbates or salycilates, alkyl esters of natural (fatty or not) acids, Sclareolide, spirolactones, allylic ester, di alkyl diesters, (un)substituted benzoic esters, and β-γ unsaturated esters. In particular, the substrate can be selected from the group consisting of sclareolide, $C_9$-$C_{15}$ spirolactones and $C_1$-$C_4$ alkyl esters of 4-methyl-6-(2,6,6-trimethyl-1-cyclohexen-1-yl)-3-hexenoic acid. One can also cite the di alkyl esters of 1,4-dicarboxylate-cyclohexane, the di $C_{1-5}$ alkyl esters of the $C_{2-10}$ alkanediyl-dicarboxylates, $C_{1-5}$ alkyl cyclopropanecarboxylates, mono-, di- or tri-methoxybenzoic esters.

The process of the invention is characterized by the use, as catalyst or pre-catalyst (hereinafter referred to as complexes unless specified otherwise), of a ruthenium complex as described above. The complex can be in the form of an ionic or neutral species.

According to an embodiment of the invention, the ruthenium complex can be of the general formula $$[Ru(L2)_b(L')_aY_2] \quad (1)$$

wherein L2 represents a bidentate ligand wherein the coordinating groups consist of one amino or imino group and one phosphino group;

L' represents a $C_3$-$C_{70}$ mono-phosphine (L1-P) or a molecule of solvent (L1-S);

b is 1 and a is 1 or 2 or b is 2 and a is 0; and each Y represents, simultaneously or independently, CO, a hydrogen or halogen atom, a hydroxyl group, or a $C_1$-$C_6$ alkoxy or carboxylic radical. Alternatively, Y may also represent a $BH_4$ or $AlH_4$ group.

In a particular embodiment of the invention the L2 ligand may be a $C_4$-$C_{40}$ compound.

In a particular embodiment of the invention, in formula (1), each Y represents, simultaneously or independently, a hydrogen or chlorine atom, a hydroxy radical, a $C_1$ to $C_6$ alkoxy radical, such as a methoxy, ethoxy or isopropoxy radical, or a $C_1$ to $C_6$ acyloxy radical such as a $CH_3COO$ or $CH_3CH_2COO$ radical. More preferably, each Y represents, simultaneously or independently, a hydrogen or chlorine atom, a methoxy, ethoxy or isopropoxy radical, or a $CH_3COO$ or $CH_3CH_2COO$ radical.

Y may also be a solvent, the term "solvent" has to be understood according to the usual meaning in the art and includes compounds used as diluent in the preparation of the complex or during the invention's process, non limiting examples are dimethylsulfoxide, acetonitrile, dimethylformamide, an alcohol (e.g. an $C_1$-$C_4$ alcohol), or also THF, acetone, pyridine or a $C_3$-$C_8$ ester or the substrate of the invention's process.

According to a particular embodiment of the invention, there can be used as complex a compound of one of the formulae $$[Ru(L2)_2Y_2] \quad (2)$$

$$[Ru(L2)(L1\text{-}P)_c(L1\text{-}S)_{2\text{-}c}Y_2] \quad (2')$$

wherein L2 and Y have the meaning indicated above, c is 1 or 2, and c' is 0, 1 or 2.

The complexes of formula (2) represent a preferred embodiment of the invention.

According to any one of the above-mentioned embodiment, the bidentate ligand L2 can be a compound of one of the formulae

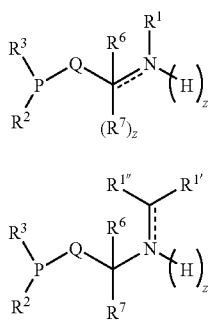

(2-A)

(2-A')

wherein the dotted line indicates a single or double bond;

z is 0 or 1 when the carbon-nitrogen bond with the dotted line represents a single or double bond respectively;

$R^1$ represents a hydrogen atom, a linear, branched or cyclic $C_1$ to $C_{10}$ alkyl or alkenyl group optionally substituted;

$R^{1'}$ and $R^{1''}$, when taken separately, represents a hydrogen atom, a linear, branched or cyclic $C_1$ to $C_9$ alkyl or alkenyl group optionally substituted or a $C_6$ to $C_{10}$ aromatic group optionally substituted; the $R^{1'}$ or $R^{1''}$, when taken together, form a saturated or unsaturated ring optionally substituted, having 5 to 12 atoms and including the carbon atom to which the $R^{1'}$ and $R^{1''}$ groups are bonded;

$R^2$ and $R^3$, when taken separately, represent, simultaneously or independently, a linear, branched or cyclic $C_1$ to $C_8$ alkyl or alkenyl group optionally substituted, a $C_6$ to $C_{10}$ aromatic group optionally substituted, or an $OR^{2'}$ or $NR^{2'}R^{3'}$ group, $R^{2'}$ and $R^{3'}$ being a $C_1$ to $C_8$ alkyl or alkenyl group; the groups $R^2$ and $R^3$, when taken together, may form a saturated or unsaturated ring optionally substituted, having 5 to 10 atoms and including the phosphorus atom to which the $R^2$ and $R^3$ groups are bonded;

$R^6$ and $R^7$ represent, simultaneously or independently, a hydrogen atom, a linear, branched or cyclic $C_1$ to $C_{10}$ alkyl or alkenyl group optionally substituted, a $C_6$-$C_{10}$ aromatic group optionally substituted, or an $OR^{4'}$ or $NR^{4'}R^{5'}$ group, $R^{4'}$ and $R^{5'}$ being a linear, branched or cyclic $C_1$ to $C_{10}$ alkyl or alkenyl group; $R^6$ and $R^1$ or $R^6$ and $R^{1''}$, taken together, may form a saturated or unsaturated heterocycle, optionally substituted and optionally containing one or two additional nitrogen or oxygen atoms, containing 5 to 10 atoms and including the carbon atoms and the N atom to which the $R^6$ or $R^1$, or $R^{1''}$, group are bonded respectively; and Q represents:

a group of formula

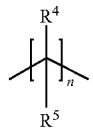

(i)

wherein n is an integer from 1 to 4, and $R^4$ and $R^5$ represent, simultaneously or independently, a hydrogen atom, a linear, branched or cyclic $C_1$ to $C_{10}$ alkyl or alkenyl group optionally substituted, a $C_6$-$C_{10}$ aromatic group optionally substituted, or an $OR^{4'}$ or $NR^{4'}R^{5'}$ group, $R^{4'}$ and $R^{5'}$ being a linear, branched or cyclic $C_1$ to $C_{10}$ alkyl or alkenyl group; two distinct $R^4$ and/or $R^5$ groups, taken together, may form a $C_5$ to $C_8$, or even up to $C_{10}$, saturated ring optionally substituted, including the carbon atoms to which each of the $R^4$ or $R^5$ group is bonded; or a group of formula

(ii)

wherein n is an integer from 2 to 4, and two distinct adjacent $R^4$ groups, taken together, form a $C_5$ to $C_8$, or even up to $C_{10}$, aromatic ring optionally substituted or a $C_5$-$C_{12}$ metallocenediyl optionally substituted, including the carbon atoms to which each of the $R^4$ group are bonded; or three distinct adjacent $R^4$ groups, taken together, form a naphthalene ring optionally substituted, including the carbon atoms to which each of the $R^4$ groups are bonded.

According to en embodiment by "aromatic group or ring" it is meant a phenyl or naphthyl derivative.

According to another embodiment of the invention, Q represents a linear $C_2$-$C_5$ alkylene radical optionally substituted, a ferrocenediyl optionally substituted or a biphenyldiyl or binaphthildiyl radical optionally substituted.

Possible substituents of $R^{1'}$, $R^{1''}$ and $R^1$ to $R^7$ and Q are one or two halogen, $C_1$ to $C_{10}$ alkoxy or polyalkyleneglycols groups, halo- or perhalo-hydrocarbon, COOR, $NR_2$, quaternary amine or R groups, wherein R is a $C_1$ to $C_6$ alkyl, or a $C_5$ to $C_{12}$ cycloalkyl, aralkyl (such as benzyl, phenethyl etc.) or aromatic group, the latter being also optionally substituted by one, two or three halogen, sulfonates groups or $C_1$-$C_8$ alkyl, alkoxy, amino, nitro, sulfonates, halo- or perhalo-hydrocarbon or ester groups. By "halo- or perhalo-hydrocarbon" it is meant groups such as $CF_3$ or $CClH_2$ for instance.

To our surprise, the ligands of formula (2-A') are new, when the dotted line represents a double bong and z is 0, at the exception of 2-(diphenylphosphino)-N-(phenylmethylene)-cyclohexanamine, and therefore are also an object of the present invention.

The complexes according to the invention having as ligand a compound of formula (2-A'), when the dotted line represents a double bong and z is 0, are also new, at the exception of dichloro[[N(Z),1R,2R]-2-(diphenylphosphino-κP)-N-

(phenylmethylene)cyclohexanamine-κN](triphenylphosphine)-Ruthenium, and are therefore also another object of the present invention.

In a particular embodiment of formula (2-A), L2 is a bidentate N—P ligand of general formula

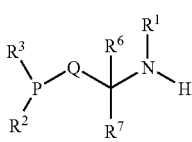

(2-B)

in which $R^1$ represents a hydrogen atom, a linear, branched or cyclic $C_1$ to $C_6$ alkyl or alkenyl group optionally substituted;

$R^2$ and $R^3$ represent, simultaneously or independently, a linear, branched or cyclic $C_1$ to $C_6$ alkyl group optionally substituted, a phenyl or naphthyl group optionally substituted; or the groups $R^2$ and $R^3$, taken together, form a saturated or unsaturated ring optionally substituted, having 5, 6 or 7 atoms and including the phosphorus atom to which the $R^2$ and $R^3$ groups are bonded;

$R^6$ and $R^7$ represent, simultaneously or independently, a hydrogen atom, a linear or branched $C_1$ to $C_4$ alkyl group optionally substituted, a phenyl ring optionally substituted; $R^6$ and $R^1$, taken together, may form a saturated or unsaturated heterocycle, optionally substituted and optionally containing one additional nitrogen or oxygen atoms, containing 5 or 6 atoms and including the carbon atoms and the N atom to which the $R^6$ or $R^1$ group are bonded respectively; and Q represents:

a group of formula

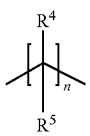

(iii)

wherein n is an integer from 2 or 3, and $R^4$ and $R^5$ represent, simultaneously or independently, a hydrogen atom, a linear or branched $C_1$ to $C_4$ alkyl group optionally substituted, a phenyl ring optionally substituted; or two distinct $R^4$ and/or $R^5$ groups, taken together, form a $C_5$ to $C_{10}$ saturated ring optionally substituted including the carbon atoms to which each of the $R^4$ or $R^5$ group is bonded; or a group of formula

(iv)

wherein n is an integer from 1 to 3, and two distinct adjacent $R^4$ groups, taken together, form a $C_5$ to $C_{10}$ aromatic ring optionally substituted or a $C_5$-$C_{12}$ ferrocenediyl optionally substituted, including the carbon atoms to which each of the $R^4$ group are bonded; or three distinct adjacent $R^4$ groups, taken together, form a naphthalene ring optionally substituted, including the carbon atoms to which each of the $R^4$ group are bonded.

Possible substituents of $R^1$ to $R^7$, in particular when the groups are or contain phenyl groups or moieties, are one or two halogen, $CF_3$ groups or $C_1$ to $C_5$ alkoxy or polyalkyleneglycols groups, COOR, $NR_2$ or R groups, wherein R is a $C_1$ to $C_4$ alkyl, or a $C_{5-6}$ cycloalkyl, aralkyl or aromatic group, the latter being also optionally substituted as above defined.

A particular embodiment of formula (2-B) is represented by formula (2-C) or (2-D)

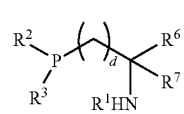

(2-C)

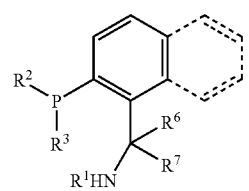

(2-D)

wherein the dotted lines in formula (2-D) indicate the presence of a phenyl or a naphthyl group;

d represents 1 or 2;

$R^1$ represents a hydrogen atom or a $C_1$ to $C_4$ linear or branched alkyl group possibly substituted;

$R^2$ and $R^3$ represent a linear, branched or cyclic $C_1$ to $C_6$ alkyl group optionally substituted or an phenyl group optionally substituted; and $R^6$ and $R^7$ represent, simultaneously or independently, a hydrogen atom, a linear or branched $C_1$ to $C_4$ alkyl group optionally substituted, or an phenyl group optionally substituted; or $R^6$ and $R^1$, taken together, form a saturated heterocycle, optionally substituted and optionally containing an additional nitrogen or oxygen atoms, such as a 2-pyrrolidine, a 2-piperidine or a 2-morpholine.

Possible substituents of $R^1$ to $R^3$, $R^6$ and $R^7$, in particular when the groups are or contain phenyl groups or moieties, are one or two halogen, $C_1$ to $C_5$ alkoxy or polyalkyleneglycols groups, COOR, $NR_2$ or R groups wherein R is a $C_1$ to $C_4$ alkyl, or a $C_{5-6}$ cycloalkyl, aralkyl or aromatic group, the latter being also optionally substituted as defined above.

In an alternative embodiment, the ligand of formula (2-A) is a bidentate N—P ligand of general formula

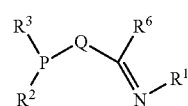

(2-E)

in which Q, $R^1$, $R^2$, $R^3$ are defined as for formula (2-B) or (2-D);

$R^6$ represents a hydrogen atom, a linear or branched $C_1$ to $C_4$ alkyl group or an phenyl group optionally substituted; or $R^6$, when taken together with $R^1$, forms a $C_3$-$C_9$ C═N function-containing heterocycle optionally substituted and optionally containing one additional nitrogen or oxygen atom.

Possible substituents of Q and $R^1$ to $R^6$, in particular when the groups are or contain phenyl groups or moieties, are one or two halogen, $CF_3$ groups or $C_1$ to $C_5$ alkoxy or polyalkyleneglycols groups, $C_1$ to $C_4$ alkyl groups, or $C_5$ to $C_{10}$ cycloalkyl, aralkyl or phenyl groups, the latter being also optionally substituted as defined above.

Alternatively one may use a complex wherein the ligand of formula (2-A') is a bidentate N—P ligand of general formula

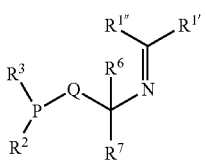

(2-E')

wherein $R^2$, $R^3$, $R^6$ and $R^7$ are as defined for (2-B) or (2-D), Q is defined as in formula (2-B); and $R^{1'}$ and $R^{1''}$, when taken separately, represents a hydrogen atom, a linear, branched or cyclic $C_1$ to $C_6$ alkyl group optionally substituted or a phenyl group optionally substituted; or the $R^{1'}$ or $R^{1''}$, when taken together, form a saturated ring optionally substituted, having 5 to 7 atoms and including the carbon atom to which the $R^{1'}$ and $R^{1''}$ groups are bonded; $R^6$ and $R^{1''}$, taken together, may form a saturated or unsaturated heterocycle, optionally substituted and optionally containing one or two additional nitrogen or oxygen atoms, containing 5 or 6 atoms and including the carbon atoms and the N atom to which the $R^6$ or $R^{1''}$, group are bonded respectively.

Alternatively, yet in the embodiments, $R^{1'}$ and $R^{1''}$, when taken separately, represents a hydrogen atom, a linear or branched $C_1$ to $C_4$ alkyl group optionally substituted or a phenyl group optionally substituted; or the $R^{1'}$ or $R^{1''}$, when taken together, form a saturated ring optionally substituted, having 5 to 7 atoms and including the carbon atom to which the $R^{1'}$ and $R^{1''}$ groups are bonded.

Possible substituents of $R^{1'}$, $R^{1''}$, $R^2$, $R^3$, Q, $R^6$ and $R^7$, in particular when the groups are or contain phenyl groups or moieties, are one or two halogen, $CF_3$ groups or $C_1$ to $C_5$ alkoxy or polyalkyleneglycols groups, $C_1$ to $C_4$ alkyl groups, or $C_5$ to $C_{10}$ cycloalkyl, aralkyl or phenyl groups, the latter being also optionally substituted as above defined.

It is understood that, in any of the above embodiments, the ferrocenediyl, as well as the metallocenediyl above mentioned, can be in the form of a ferrocene-1,1'-diyl or of a ferrocene-1,2-diyl.

A particular embodiment of formula (2-E) is a ligand of formula (2-F), (2-F'), (2-G) or (2-G')

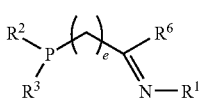

(2-F)

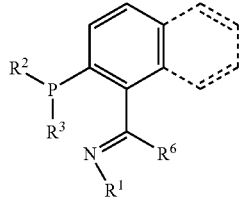

(2-G)

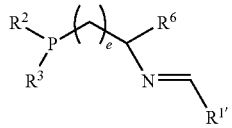

(2-F')

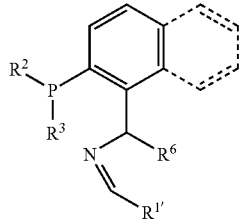

(2-G')

wherein the dotted lines in formula (2-G) or (2-G') indicate the presence of a phenyl or a naphthyl group; e represents 1 or 2, and in particular 1;

$R^1$, $R^2$, $R^3$, are defined as in formula (2-E), $R^{1'}$ is defined as $R^1$ in formula (2-E); and $R^6$ represents a hydrogen atom, a linear or branched $C_1$ to $C_4$ alkyl group optionally substituted, or a phenyl group optionally substituted; or $R^6$, when taken together with $R^1$, forms a $C_3$-$C_9$ C=N function-containing heterocycle optionally substituted and optionally containing one additional nitrogen or oxygen atom such as a 2-pyridyl, a 1-oxazolinyl, a 2-imidazolyl or a 2-isoquinolinyl group.

Possible substituents of $R^1$ to $R^3$ and $R^6$, in particular when the groups are or contains phenyl groups or moieties, are one or two halogen, $C_1$ to $C_5$ alkoxy or polyalkyleneglycols groups, $C_1$ to $C_4$ alkyl groups, or $C_5$ to $C_{10}$ cycloalkyl, aralkyl or phenyl groups, the latter being also optionally substituted as above defined.

In all the above embodiments when it is the that "$R^2$ and $R^3$, when taken together, may form a saturated or unsaturated ring ...", one can cite a trivial example of such type of $R^2$ and $R^3$ taken together the following: diphenyl or dinaphthyl group (which will form an unsaturated 5 atom ring) or a —$(CH_2)_5$— group (which will form a saturated 6 atom ring).

Furthermore, in all the above embodiments, a particularly appreciated mode of realization is the one where the $R^2$ and $R^3$ groups are aromatic groups optionally substituted.

In a particular embodiment of the invention the L' ligand may be a preferably $C_3$-$C_{30}$ mono-phosphine, and in particular of formula $PR^d_3$, wherein $R^d$ is a $C_1$-$C_{12}$ group, such as linear, branched or cyclic alkyl, alkoxy or aryloxy group optionally substituted, substituted or unsubstituted phenyl, diphenyl or naphthyl or di-naphthyl group, or a solvent such as THF, acetone, pyridine an $C_3$-$C_8$ ester or an $C_1$-$C_4$ alcohol. Possible substituents are those cited above for L2.

The processes of the invention are particularly attractive when are used complexes of the (2) $[Ru(L2)_2Y_2]$ wherein Y represents H or Cl, and L2 represents a ligand of the formula (2-H):

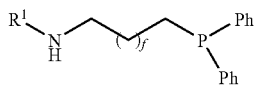

(2-H)

wherein $R^1$ represents a hydrogen atom or a methyl group, Ph is phenyl radical.

The ligands described above can be obtained by applying standard general methods which are well known in the state of the art and by the person skilled in the art. Therefore, their preparation does not require a specific description. For example one may revert to WO 02/22526.

In a general way, the complexes of formula (1) can be prepared and isolated prior to their use in the process according to the general methods described in the literature. A method is described in the Example.

Moreover, the complexes can be prepared in situ, by several methods, in the hydrogenation medium, without isolation or purification, just before their use.

One of the possible procedures to advantageously prepare in situ a complex of formula (1) consists in reacting an appropriate Ru complex of formula [Ru("diene")("allyl")$_2$], wherein "diene" represents a cyclic or linear hydrocarbon containing two carbon-carbon double bonds, conjugated or not, such as for example 1,5-cyclooctadiene (COD) or norbornadiene, and "allyl" represents a linear or branched $C_3$ to $C_8$ hydrocarbon radical containing one carbon-carbon double bond such as methylallyl or allyl, with a non coordinating acid such as $HBF_4.Et_2O$, and then treating the resulting solution with the required amount of a ligands L2, and if necessary of ligand L', such as defined previously, to give a solution of a catalyst according to formula (1). Furthermore, the mixture thus obtained can also be treated with a base in the presence of a primary or secondary alcohol. Furthermore, the complexes of formula (I) can be prepared by reacting an appropriate Ru complex such as, $[RuCl_2(PPh_3)_3]$, $[RuCl_2(cod)]$ or $[RuCl_2(arene)]_2$ with the required amount of a ligands L2, and if necessary of ligand L', such as defined previously (cod representing a cyclooctadiene and arene being e.g. a benzene or naphthalene).

It is also understood that the complex of formula (I) can also be obtained in situ from complexes which have a similar formula or are cationic or anionic, for examples a complex (I) wherein Y has another meaning or a complex of formula $[Ru(L2)_2(solvent)_2](Anion)_2$, wherein the anion is a non-coordinating one, which in presence of, for example an alcohol and a base, are converted into a compound of formula (I).

To carry out the processes of the invention it is required also to use a base. The base can be the substrate itself, if the latter is basic, a corresponding alcoholate or any base having preferentially a $pK_a$ above 11. According to a particular embodiment of the invention the base may have a $pK_a$ above 14. It is also understood that preferably the base does not reduce itself a substrate of formula (I). As non-limiting examples one may cite the following type of base: alcoholate, hydroxides, alkaline or alkaline-earth carbonates, phosphazines, amides, basic alox, siliconates (i.e. silicium derivatives having $SiO^-$ or $SiRO^-$ groups), hydrides such as $NaBH_4$, NaH or KH.

One can cite, as non-limiting examples, alkaline or alkaline-earth metal carbonates, such as cesium carbonate, an alkaline or alkaline-earth metal hydroxides, $C_{1-10}$ amidures, $C_{10-26}$ phosphazine or an alcoholate of formula $(R^{13}O)_2M$ or $R^{13}OM'$, wherein M is an alkaline-earth metal, M' is an alkaline metal or an ammonium $NR^{14}{}_4{}^+$, $R^{13}$ stands for hydrogen or a $C_1$ to $C_6$ linear or branched alkyl radical and $R^{14}$ stands for a $C_1$ to $C_{10}$ linear or branched alkyl radical, such as sodium or potassium alcoholates. Of course, other suitable bases can be used.

According to an embodiment of the invention, the base is an alkaline alcoholate of formula $R^{13}OM'$.

As previously mentioned the processes of the invention consist in the hydrogenation of a substrate using a ruthenium complex and a base. A typical process implies the mixture of the substrate with the ruthenium complex, a base and optionally a solvent, and then treating such a mixture with molecular hydrogen at a chosen pressure and temperature.

The complexes of the invention, an essential parameter of the process, can be added to the reaction medium in a large range of concentrations. As non-limiting examples, one can cite as complex concentration values those ranging from 50 ppm to 50000 ppm, relative to the amount of substrate. Preferably, the complex concentration will be comprised between 100 and 20000 ppm. It goes without saying that the optimum concentration of complex will depend, as the person skilled in the art knows, on the nature of the latter, on the nature of the substrate and on the pressure of $H_2$ used during the process, as well as the desired time of reaction.

Useful quantities of base, added to the reaction mixture, may be comprised in a relatively large range. One can cite, as non-limiting examples, ranges between 5 to 50000 molar equivalents, relative to the complex (e.g. base/com=5 to 50000), preferably 20 to 2000, and even more preferably between 50 and 1000 molar equivalents.

The hydrogenation reaction can be carried out in the presence or absence of a solvent. When a solvent is required or used for practical reasons, then any solvent current in hydrogenation reactions can be used for the purposes of the invention. Non-limiting examples include aromatic solvents such as toluene or xylene, hydrocarbon solvents such as hexane or cyclohexane, ethers such as tetrahydrofuran or MTBE, polar solvents such as primary or secondary alcohols such as isopropanol or ethanol, or mixtures thereof. The choice of the solvent is a function of the nature of the complex and the person skilled in the art is well able to select the solvent most convenient in each case to optimize the hydrogenation reaction.

In the hydrogenation process of the invention, the reaction can be carried out at a $H_2$ pressure comprised between $10^5$ Pa and $80 \times 10^5$ Pa (1 to 80 bars) or even more if desired. Again, a person skilled in the art is well able to adjust the pressure as a function of the catalyst load and of the dilution of the substrate in the solvent. As examples, one can cite typical pressures of 1 to $50 \times 10^5$ Pa (1 to 50 bar).

The temperature at which the hydrogenation can be carried out is comprised between 0° C. and 120° C., more preferably in the range of between 50° C. and 100° C. Of course, a person skilled in the art is also able to select the preferred temperature as a function of the melting and boiling point of the starting and final products as well as the desired time of reaction or conversion.

EXAMPLES

The invention will now be described in further detail by way of the following examples, wherein the temperatures are indicated in degrees centigrade and the abbreviations have the usual meaning in the art.

All the procedures described hereafter have been carried out under an inert atmosphere unless stated otherwise. Hydrogenations were carried out in open glass tubes placed inside a stainless steel autoclave. H$_2$ gas (99.99990%) was used as received. All substrates and solvents were distilled from appropriate drying agents under Ar. NMR spectra were recorded on a Bruker AM-400 ($^1$H at 400.1 MHz, $^{13}$C at 100.6 MHz, and $^{31}$P at 161.9 MHz) spectrometer and normally measured at 300 K, in CDCl$_3$ unless indicated otherwise. Chemical shifts are listed in ppm.

Example 1

A) Preparation of Complexes [RuCl$_2$(L-1)$_n$], [RuCl$_2$(L-2)$_2$], [RuCl$_2$(L-4)$_2$]

a) Preparation of the Complex Dichloro bis[2-(Diphenylphosphino)ethylamine]Ruthenium ([RuCl$_2$(L-1)$_2$])

Under argon, a round-bottomed Schlenck flask, equipped with a magnetic stirring bar, was charged with RuCl$_2$(PPh$_3$)$_3$ (418.6 mg, 0.436 mmol) and toluene (6 mL). Then under stirring, a solution of 2-(diphenylphosphino)ethylamine (201.6 mg, 0.879 mmol) in toluene (3 mL) was added, more toluene (3 mL) was added to rinse. Then the dark-brown solution was heated in an oil bath at 100° C. for six hours. The resulting yellow suspension was cooled to room temperature, and filtered under argon. The yellow solid was rinsed with toluene until the filtrate was colourless and then dried in-vacuo. The desired complex (258.4 mg, 0.41 mmol, 94%) was then collected as a pale-yellow solid. $^{31}$P{$^1$H}-NMR analysis showed the presence of two species the major one being the trans-chloride-cis-phosphorous complex (75%) and the minor one being the cis-chloride-cis-phosphorous complex (25%).

$^1$H-NMR (CD$_2$Cl$_2$): δ (A) 7.24 (m, 4H), 7.16 (m, 8H), 7.07 (m, 8H), 3.78 (brs, 4H, NH$_2$), 3.22 (m, 4H), 2.70 (brs, 4H).

$^{13}$C{$^1$H}-NMR (CD$_2$Cl$_2$): δ (A) 137.1 (Carom), 133.9 (t, J=5 Hz, CHarom), 129.2 (CHarom), 127.6 (t, J=5 Hz, CHarom), 41.9 (CH$_2$), 33.3 (t, J=13.5 Hz, CH$_2$).

$^{31}$P{$^1$H}-NMR (CD$_2$Cl$_2$): A (75%) δ=62.6 ppm (s); B (25%) β=67.5 ppm (d, J=32 Hz), 56.2 ppm (d, J=32 Hz).

b) Preparation of the Complex Dichloro [2-(Diphenylphosphino)ethylamine][triphenylphosphine]Ruthenium ([RuCl$_2$(L-1)(PPh$_3$)])

Under argon, a round-bottomed Schlenck flask, equipped with a magnetic stirring bar, was charged with RuCl$_2$(PPh$_3$)$_3$ (20.0 g, 20.9 mmol) and THF (160 mL). Then under stirring, neat 2-(diphenylphosphino)ethylamine (4.83 g, 21.1 mmol) was added over five minutes. Next, the reaction mixture was stirred at room temperature for three hours. During that time, the dark ruthenium suspension quickly dissolves before precipitating back as a pink solid. Reaction mixture was then filtered under nitrogen (dark filtrate). The obtained solid was washed with THF (3×40 ml) and then MTBE. The pink solid was then dried in-vacuo overnight to afford the ruthenium complex as a pink solid (14.0 g, 21 mmol).

$^{31}$P{$^1$H}-NMR analysis showed the presence of several ruthenium species, and also showed the presence of free triphenylphosphine probably liberated by product evolution in solution, as the solid was washed several times with THF.

$^{31}$P{$^1$H}-NMR (CD$_2$Cl$_2$): δ=59.96 (d, J=30.7 Hz), 59.46 (t, J=35.1 Hz), 58.51 (s), 44.64 (d, J=30.7 Hz), 44.29 (d, J=30.7 Hz), −4.84 (s, free PPh$_3$).

c) Preparation of the Complex Dichloro bis[3-(Diphenylphosphino)-1-propylamine]Ruthenium ([RuCl2(L-2)$_2$])

Under argon, a round-bottomed Schlenck flask, equipped with a magnetic stirring bar, was charged with RuCl$_2$(PPh$_3$)$_3$ (1.028 g, 1.07 mmol) and with a solution of 3-(diphenylphosphino)-1-propylamine (566.8 mg, 2.33 mmol) in toluene (5 mL). More toluene (5 mL) was added to rinse. Then the dark-brown solution was heated in an oil bath at 100° C. for 16 h. The resulting brick-orange suspension was cooled to room temperature, and added to pentane (50 mL) with stirring. The yellow solid was collected by filtration, washed with pentane (2×3 mL) and dried in vacuo to provide the desired complex (672.6 mg, 1.02 mmol, 95%) as a yellow-mustard solid. $^{31}$P{$^1$H}-NMR analysis showed the presence of two species.

$^1$H-NMR (CD$_2$Cl$_2$): δ (A) 7.19 (t, J=7.2 Hz, 4H), 7.14 (m, 8H), 7.05 (t, J=7.2 Hz, 8H), 3.28 (brs, 4H), 3.02 (brs, 4H), 2.66 (m, 4H), 2.0 (m, 4H).

$^{13}$C-NMR (CD$_2$Cl$_2$): δ (A) 138.4 (t, J=19.2 Hz, Carom), 134.2 (t, J=4.8 Hz, CHarom), 129.0 (CHarom), 127.5 (t, J=4.8 Hz, CHarom), 41.3 (CH$_2$), 26.9 (t, J=13.6 Hz, CH$_2$), 24.7 (CH$_2$).

$^{31}$P{$^1$H}-NMR (CD$_2$Cl$_2$): A (82%) δ=33.5 ppm (s), B (18%) δ=49.8 ppm (s).

d) Preparation of the Complex Dichloro bis-2-[2-(diisobutylphosphino)ethyl]pyridine Ruthenium ([RuCl$_2$(L-4)$_2$])

Under argon, a round-bottomed Schlenck flask, equipped with a magnetic stirring bar, was charged with RuCl$_2$(PPh$_3$)$_3$ (535.2 mg, 0.56 mmol) and with a solution of 2-[2-(diisobutylphosphino)ethyl]pyridine (306.5 mg, 1.22 mmol) in toluene (3 mL). More toluene (2×1 mL) was added to rinse. Then the dark-brown solution was heated in an oil bath at 100° C. for 6 h. The resulting red solution was cooled to room temperature, and the solvent removed in vacuo to give an orange solid. The solid was dissolved in CH$_2$Cl$_2$ (3 mL), MeOH (15 mL) was added and the solution was concentrated in vacuo until a yellow precipitate forms. The solid was recovered by filtration, washed with MeOH (1 mL) and dried in vacuo to give the desired complex (458.9 mg). $^{31}$P{$^1$H}-NMR analysis showed the presence of free PPh$_3$ (44 wt %). The solid (425.8 mg) was dissolved in CH$_2$Cl$_2$ (10 mL), and the solution added to a suspension of CuCl (86.1 mg, 0.87 mmol) in CH$_2$Cl$_2$ (10 mL). More CH$_2$Cl$_2$ (5 mL) was added to rinse. The solution was stirred for 5 min. and then the solvent was removed in vacuo. The resulting solid was triturated with a mixture of hexane (25 mL)/CH$_2$Cl$_2$ (5 mL) and then filtered over a pad of Celite. The pad was further washed with hexane/CH$_2$Cl$_2$ (5/1, 3×5 mL). The combined filtrate was concentrated in vacuo until precipitation of a yellow solid occurred. The solid was recovered by filtration and dried in vacuo to give the desired complex (152.1 mg, 0.22 mmol, 40%) as a yellow solid, free of triphenylphosphine.

$^1$H-NMR (CD$_2$Cl$_2$): δ 8.18 (d, J=5.9 Hz, 1H), 7.69 (ddd, J=1.5, 7.2, 7.7 Hz, 1H), 7.2 (d, J=7.2 Hz, 1H), 6.84 (ddd, J=1.5, 5.9, 7.2 Hz, 1H), 4.5 (brs, 1H), 2.9 (brs, 1H), 2.5 (brs, 1H), 2.3 (brs, 2H), 2.1 (brs, 1H), 1.99 (brs, 1H), 1.68 (brd, J=14 Hz, 2H), 1.55 (brs, 1H), 0.8-1.2 (brm, 12H).

¹³C-NMR (CD₂Cl₂): δ 167.6 (Carom), 158.5 (CHarom), 136.9 (CHarom), 124.2 (CHarom), 121.5 (CHarom), 40.0 (brs, CH₂), 36.6 (brs, CH₂), 33.2 (CH₂), 26.1 (CH₃), 25.7 (CH₃), 25.3 (CH), 19.7 (t, J=10.4 Hz, CH₂).

³¹P{¹H}-NMR (CD₂Cl₂): δ=40.2 ppm (s).

B) Preparation of Imino-Phosphine Ligands (L-6 to L-10)

a) Preparation of N-[2-(diphenylphosphino)ethyl]-N-[phenylmethylene]amine (L-6)

Under argon, a solution of 2-diphenylphosphino-ethylamine (590.3 mg, 2.57 mmol) and benzaldehyde (275.0 mg, 2.59 mmol) in ethanol (15 mL) was heated at 65° C. (oil bath) for 4 h. Then, the solvent was removed in-vacuo to give the desired product (>98% by ¹H-NMR) as a colourless oil which solidified on standing (733.9 mg, 2.31 mmol, 90%).

¹H-NMR (CD₂Cl₂): δ 8.2 (s, 1H, CH=N), 7.68-7.62 (m, 2H), 7.49-7.43 (m, 4H), 7.4-7.28 (m, 9H), 3.71 (ddt, J=1, 8, 9 Hz, 2H), 2.45 (ap t, J=8 Hz, 2H).

¹³C-NMR (CD₂Cl₂): δ 161.3 (CH C=N), 139.2 (d, J=12.9 Hz, Carom), 136.7 (Carom), 133.1 (d, J=18.6 Hz, CHarom), 130.9 (CHarom), 128.91 (CHarom), 128.86 (CHarom), 128.8 (d, J=6.5 Hz, CHarom), 128.4 (CHarom), 58.7 (d, J=21 Hz, CH₂), 30.1 (d, J=12.9 Hz, CH₂).

³¹P{¹H}-NMR (CD₂Cl₂): δ=−18.5 ppm (s).

b) Preparation of N-[(3,5-Dimethylphenyl)methylene]-N-[2-(diphenylphosphino)ethyl]amine (L-7)

Under argon, a solution of 2-diphenylphosphino-ethylamine (652.2 mg, 2.84 mmol) and 3,5-dimethyl-benzaldehyde (387.4 mg, 2.89 mmol) in ethanol (15 mL) was heated at 65° C. (oil bath) for 4 h. Then, the solvent was removed in-vacuo to give the desired product (>98% by ¹H-NMR) as a colourless oil (993.2 mg, 2.8 mmmol, quantitative).

¹H-NMR (CD₂Cl₂): δ 8.13 (s, 1H, CH=N), 7.48-7.42 (m, 4H), 7.35-7.29 (m, 6H), 7.25 (s, 2H), 7.04 (s, 1H), 3.68 (dq, J=1.3, 7.7 Hz, 2H), 2.44 (t, J=7.7 Hz, 2H), 2.3 (s, 6H).

¹³C-NMR (CD₂Cl₂): δ 161.7 (CH C=N), 139.2 (d, J=13.7 arom), 138.5 (Carom), 136.6 (Carom), 133.1 (d, J=19.4 Harom), 132.6 (CHarom), 128.9 (CHarom), 128.8 (d, J=6.5 CHarom), 126.2 (CHarom), 58.7 (d, J=21 Hz, CH₂), 30.2 (d, J=12.9 Hz, CH₂), 21.2 (CH₃).

³¹P{¹H}-NMR (CD₂Cl₂): δ=−18.5 ppm (s).

c) Preparation of N-[cyclohexylmethylene]-N-[2-(diphenylphosphino)ethyl]amine (L-8)

Under argon, a solution of 2-diphenylphosphino-ethylamine (619.0 mg, 2.7 mmol) and cyclohexane carbaldehyde (306.2 mg, 2.73 mmol) in ethanol (15 mL) was heated at 65° C. (oil bath) for 4 h. Then, the solvent was removed in-vacuo to give the desired product (>98% by ¹H-NMR) as a colourless liquid (880.5 mg, 2.7 mmmol, quantitative).

¹H-NMR (CD₂Cl₂): δ 7.47-7.39 (m, 5H), 7.35-7.28 (m, 6H), 3.42 (q, J=8.2 Hz, 2H), 2.32 (t, J=7.7 Hz, 2H), 2.12-2.01 (m, 1H), 1.77-1.67 (m, 4H), 1.67-1.58 (m, 1H), 1.34-1.1 (5H).

¹³C-NMR (CD₂Cl₂): δ 169.2 (CH=N), 139.2 (d, J=13.7 Hz, Carom), 133.1 (d, J=19.4 Hz, CHarom), 128.9 (CHarom), 128.8 (d, J=6.5 Hz, CHarom), 58.5 (d, J=20.2 Hz, CH₂), 43.6 (CH), 30.2 (d, J=12.1 Hz, CH₂), 29.9 (CH₂), 36.5 (CH₂), 25.9 (CH₂).

³¹P{¹H}-NMR (CD₂Cl₂): δ=−18.9 ppm (s).

d) Preparation of N-benzylidene-N-[3-(diphenylphosphino)propyl]amine (L-9)

Under argon, a solution of 3-diphenylphosphino-propylamine (631.2 mg, 2.6 mmol) and benzaldehyde (278.1 mg, 2.6 mmol) in ethanol (15 mL) was heated at 65° C. (oil bath) for 4 h. Then, the solvent was removed in-vacuo to give the desired product (>98% by ¹H-NMR) as a white solid (822.3 mg, 2.5 mmmol, 96%).

¹H-NMR (CD₂Cl₂): δ 8.24 (s, CH=N), 7.72-7.68 (m, 2H), 7.45-7.37 (m, 7H), 7.33-7.28 (m, 6H), 3.66 (dt, J=1.0, 6.7 Hz, 2H), 2.13 (dd, J=5.4, 7.9, 10.5 Hz, 2H), 1.85-1.75 (m, 2H).

¹³C-NMR (CD₂Cl₂): δ 161.3 (CH C=N), 139.9 (d, J=13.7 Hz, Carom), 136.9 (Carom), 133.1 (d, J=18.6 Hz, CHarom), 130.8 (CHarom), 128.9 (CHarom), 128.8 (CHarom), 128.7 (d, J=6.5 Hz, CHarom), 128.4 (CHarom), 62.5 (d, J=12.9 Hz, CH₂), 27.8 (d, J=16.9 Hz, CH₂), 25.8 (d, J=11.3 Hz, CH₂).

³¹P{¹H}-NMR (CD₂Cl₂): δ=−15.9 ppm (s).

e) Preparation of N-benzylidene-N-[3-(diisobutylphosphino)propyl]amine (L-10)

Under argon, a solution of 3-diisobutylphosphino-propylamine (428.5 mg, 2.11 mmol) and benzaldehyde (226.9 mg, 2.14 mmol) in ethanol (15 mL) was heated at 65° C. (oil bath) for 4 h. Then, the solvent was removed in-vacuo to give the desired product (>98% by ¹H-NMR) as a colourless liquid (614.1 mg, 2.1 mmol, quantitative).

¹H-NMR (CD₂Cl₂): δ 8.27 (s, 1H), 7.73-7.68 (m, 2H), 7.43-7.38 (m, 3H), 3.63 (t, J=6.7 Hz, 2H), 1.82-1.74 (m, 2H), 1.73-1.64 (m, 2H), 1.41-1.37 (m, 2H), 1.35-1.22 (m, 4H), 0.98 (d, J=6.7 Hz, 6H), 0.97 (d, J=6.7 Hz, 6H).

¹³C-NMR (CD₂Cl₂): δ 160.9 (CH C=N), 136.9 (Carom), 130.7 (CHarom), 128.9 (CHarom), 128.3 (CHarom), 63.1 (d, J=11.3 Hz, CH₂), 39.5 (d, J=13.7 Hz, CH₂), 27.7 (d, J=12.9 Hz, CH₂), 26.9 (d, J=13.7 Hz, CH), 26.7 (d, J=12.9 Hz, CH₂), 24.53 (d, J=8.9 Hz, CH₃), 24.45 (d, J=8.1 Hz, CH₃).

³¹P{¹H}-NMR (CD₂Cl₂): δ=−39.6 ppm (s).

The structure of the ligands is reported in Table 1:

TABLE 1

Structure of ligands (L-1 to L-10) used in complexes of formula (1)

| structure | name |
|---|---|
| H₂N–CH₂CH₂–PPh₂ | L-1 |
| H₂N–(CH₂)₃–PPh₂ | L-2 |
| H₂N–(CH₂)₃–P(iBu)₂ | L-3 |

TABLE 1-continued

Structure of ligands (L-1 to L-10) used in complexes of formula (1)

| structure | name |
|---|---|
| (pyridine-CH₂CH₂-P(iBu)₂) | L-4 |
| (2-PPh₂-C₆H₄-CH=N-CH₂-Ph) | L-5 |
| (Ph-CH=N-CH₂CH₂-PPh₂) | L-6 |
| (3,5-dimethyl-C₆H₃-CH=N-CH₂CH₂-PPh₂) | L-7 |
| (Cy-CH=N-CH₂CH₂-PPh₂) | L-8 |
| (Ph-CH=N-CH₂CH₂CH₂-PPh₂) | L-9 |
| (Ph-CH=N-CH₂CH₂CH₂-P(iBu)₂) | L-10 |

Ligands L-1 and L-2 are commercially available (Fluka). Ligands L-3 and L-4 were prepared according to Rautenstrauch, V. et al. in WO 02/22526 A2.

C) Preparation of Complexes [RuCl2(L-6 to L-10)₂]

See below example 2b) for the in-situ generation of these complexes.

Example 2

Catalytic Hydrogenation of Various Esters Using Complexes of Formula (1)

a) Using Pre-Formed Complex

A typical catalytic hydrogenation using $RuCl_2(L-1)_2$ as pre-catalyst is described below with methyl benzoate as substrate:

Under argon, a solution of methyl benzoate (3.249 g, 24 mmol) in THF (2 mL) was added with a syringe, followed by more THF (2×1 mL), to a Keim autoclave equipped with a glass liner containing [$RuCl_2(L-1)_2$] (7.5 mg, 0.012 mmol, 0.05 mol %), solid NaOMe (128.2 mg, 2.4 mmol, 10 mol %) and THF (12.5 mL). The autoclave was pressurised with hydrogen gas at 50 bars and placed in a thermostatted oil bath set at 100° C. After 2 h 30 min, the autoclave was removed from the oil bath, and cooled in a cold-water bath. Then, the reaction mixture was diluted with citric acid 10% w/w (25 mL) and extracted with MTBE (100 mL). The organic phases was washed with aq. sat. NaCl (3×50 mL). Gas chromatography after silylation showed the following products: benzyl alcohol (97.5%), benzoic acid (2.5%). Then, the organic phase was washed successively with aq. KOH 1 M (50 mL) and aq. sat. NaCl (3×50 mL), and dried over $MgSO_4$ anh. Filtration and removal of the solvent in vacuo gave a yellow liquid (3.486 g). Purification by Kugelrohr distillation (130-140° C./8.5 mbar) gave pure benzyl alcohol (2.081 g, 19 mmol, 80%) as a colourless liquid.

$^1$H NMR ($CDCl_3$, 400 MHz): δ 7.38-7.25 (m, 5H), 4.65 (s, 2H), 2.02 (s, 1H).

$^{13}$C NMR ($CDCL_3$, 100 MHz): δ 140.9 (s), 128.6 (d), 127.6 (d), 126.9 (d), 62.3 (t).

b) Using In-Situ Formed Complex

A typical catalytic hydrogenation using in-situ formed $RuCl_2(L-6)_2$ as pre-catalyst is described below for methyl benzoate as substrate:

Under argon, a solution of methyl benzoate (2.729 g, 20 mmol) in THF (2 mL) was added with a syringe, followed by more THF (2×1 mL), to a Keim autoclave equipped with a glass liner containing [$RuCl_2$(para-cymene)]₂ (6.9 mg, 0.01 mmol, 0.05 mol %), ligand L-6 (15.4 mg, 0.05 mmol, 0.24 mol %), solid NaOMe (106.2 mg, 2 mmol, 10 mol %) and THF (6 mL). Then a solution of tridecane (338.1 mg, 1.83 mmol), as internal standard, is added in THF (2 mL), followed by more THF (2×1 mL). The autoclave was then pressurised with hydrogen gas at 50 bars and placed in a thermostatted oil bath set at 100° C. After 1 h, the autoclave was removed from the oil bath, and cooled in a cold-water bath. An aliquot (0.3 mL) was withdrawn and diluted with MTBE (5 mL). The organic phase was washed with aq. sat. NaCl (5 mL), filtered through Celite and analysed. GC yield based on the internal standard gave the yield of 81% in benzyl alcohol.

Using methyl benzoate as a test substrate several complexes with ligands described in Table 1, bases and solvent were tested under these conditions. The resulted are summarized in Table 2.

TABLE 2

Hydrogenation of methyl benzoate using [RuCl$_2$(L)n]

| Test | Complex | Com/Base | Base | Solvent | Conv. |
|---|---|---|---|---|---|
| 1 | [RuCl$_2$(PPh$_3$)$_3$] | 4000/1000000 | NaOMe | THF | 0 |
| 2 | [(RuCl$_2$(Cym))$_2$] | 500/100000 | NaOMe | THF | 0 |
| 3 | [RuCl$_2$(L-1)$_2$] | 1000/1000000 | NaOMe | THF | 0[1] |
| 4 | [RuCl$_2$(L-1)$_2$] | 1000/1000000 | NaOMe | THF | 86 |
| 5 | [RuCl$_2$(L-1)$_2$] | 1000/100000 | NaOMe | THF | 97 |
| 6 | [RuCl$_2$(L-1)$_2$] | 1000/100000 | NaOMe | THF | 98[2] |
| 7 | [RuCl$_2$(L-1)$_2$] | 500/100000 | NaOMe | THF | 98 (81)[3a] |
| 8 | [RuCl$_2$(L-1)$_2$] | 1000/100000 | NaOMe | THF | 75[4] |
| 9 | [RuCl$_2$(L-1)$_2$] | 1000/100000 | NaOMe | THF | 93[5] |
| 10 | [RuCl$_2$(L-1)$_2$] | 2000/100000 | NaOMe | THF | 32[6] |
| 11 | [RuCl$_2$(L-1)$_2$] | 1000/1000000 | NaOMe | MTBE | 87 |
| 12 | [RuCl$_2$(L-1)$_2$] | 1000/1000000 | NaOMe | Toluene | 87 |
| 13 | [RuCl$_2$(L-1)$_2$] | 1000/1000000 | NaOMe | $^i$PrOH | 87 |
| 14 | [RuCl$_2$(L-1)$_2$] | 1000/1000000 | NaOMe | EtOH | 87 |
| 15 | [RuCl$_2$(L-1)$_2$] | 1000/1000000 | NaOMe | MeOH | 20 |
| 16 | [RuCl$_2$(L-1)$_2$] | 1000/1000000 | NaOEt | THF | 83 |
| 17 | [RuCl$_2$(L-1)$_2$] | 1000/1000000 | NaO$^t$Bu | THF | 96 (85)[7] |
| 18 | [RuCl$_2$(L-1)$_2$] | 1000/1000000 | NaOH | THF | 49 |
| 19 | [RuCl$_2$(L-1)$_2$] | 5000/1000000 | NaHMDS[8] | THF | 23[9] |
| 20 | [RuCl$_2$(L-1)(PPh$_3$)] | 1000/1000000 | NaOMe | THF | 22 |
| 21 | [RuCl$_2$(L-2)$_2$] | 1000/1000000 | NaOMe | THF | 70 |
| 22 | [RuCl$_2$(L-2)$_2$] | 1000/100000 | NaOMe | THF | 54[2] |
| 23 | [RuCl$_2$(L-3)$_2$] | 500/100000 | NaOMe | THF | 6[2] |
| 24 | [RuCl$_2$(L-4)$_2$] | 500/100000 | NaOMe | THF | 7[3] |
| 25 | [RuCl$_2$(L-5)$_2$] | 500/100000 | NaOMe | THF | 31[2] |
| 27 | [RuCl$_2$(L-6)$_2$] | 500/100000 | NaOMe | THF | 81[2] |
| 28 | [RuCl$_2$(L-7)$_2$] | 500/100000 | NaOMe | THF | 91[2] |
| 29 | [RuCl$_2$(L-8)$_2$] | 500/100000 | NaOMe | THF | 82[2] |
| 30 | [RuCl$_2$(L-9)$_2$] | 500/100000 | NaOMe | THF | 11[2] |
| 31 | [RuCl$_2$(L-10)$_2$] | 500/100000 | NaOMe | THF | 8[2] |

Com/Base: molar ratio in ppm relative to the substrate.
Conv. = conversion (in %, analysed by GC) of methyl benzoate into benzyl alcohol after 1 hour. Reaction conditions: H$_2$ gas (50 bars), 100° C., solvent (1.4 M).
[1] Test performed under an atmosphere of argon.
[2] Catalyst generated in-situ with L (0.22 mol %) and [(RuCl$_2$(Cym))$_2$] (0.05 mol %). Indicated is GC yield based on internal standard.
[3] Test performed during 2 h 30 min; a) isolated yield in brackets; b) indicated is GC yield based on internal standard.
[4] Test performed at 50° C.
[5] Test performed under H$_2$ gas of 20 bars.
[6] Test performed under H$_2$ gas of 10 bars. GC yield based on internal standard in brackets.
[7] Isolated yield in brackets.
[8] NaHMDS: Sodium bis(trimethylsilyl)amide.
[9] Test performed during 2 hours.

Several others esters (see Table 3) were hydrogenated under identical conditions as reported in Table 4 with RuCl$_2$(L-1)$_2$. The reaction conditions were identical to those reported above for methyl benzoate.

TABLE 3

Structure and name of substrates used

| Substrate | Structure | Name |
|---|---|---|
| 1 | 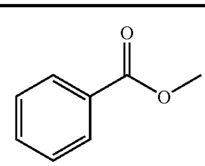 | Methyl benzoate |
| 2 | 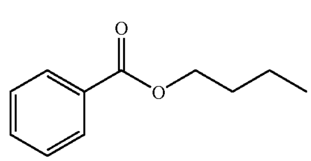 | Butyl benzoate |

TABLE 3-continued

Structure and name of substrates used

| Substrate | Structure | Name |
|---|---|---|
| 3 | 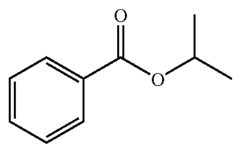 | iso-Propyl benzoate |
| 4 | 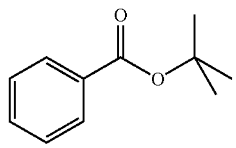 | tert-Butyl benzoate |
| 5 | 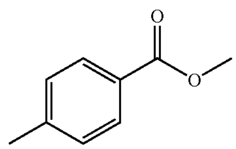 | Methyl 4-methylbenzoate |
| 6 | 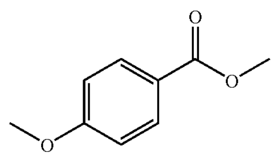 | Methyl 4-methoxybenzoate |
| 7 | 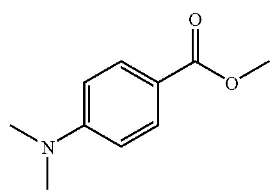 | Methyl 4-(dimethylamino)benzoate |
| 8 | 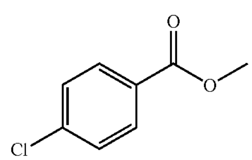 | Methyl 4-chlorobenzoate |
| 9 | 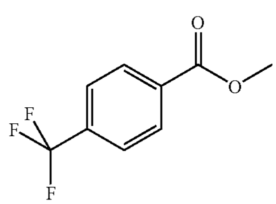 | Mehyl 4-(trifluoromethyl)benzoate |
| 10 | 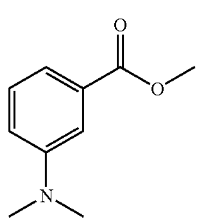 | Methyl 3-(dimethylamino)benzoate |
| 11 | 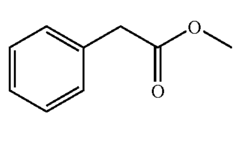 | Methyl phenylacetate |

TABLE 3-continued

Structure and name of substrates used

| Substrate | Structure | Name |
|---|---|---|
| 12 | 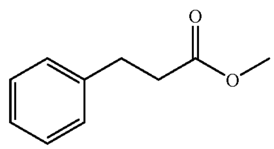 | Methyl 3-phenylpropanoate |
| 13 | 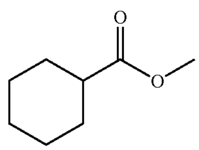 | Methyl cyclohexanecarboxylate |
| 14 | 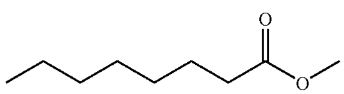 | Methyl octanoate |
| 15 | 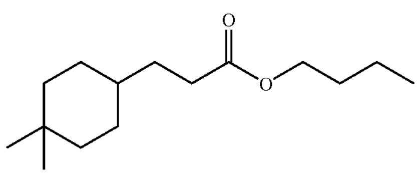 | Butyl 3-(4,4-dimethylcyclohexyl) propanoate |
| 16 | 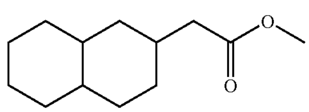 | Methyl perhydro-2-naphthylacetate |
| 17 | 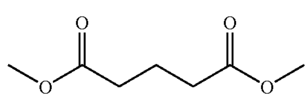 | Dimethyl pentanedioate |
| 18 | 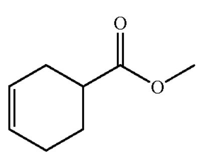 | Methyl 3-cyclohexene-1-carboxylate |
| 19 | 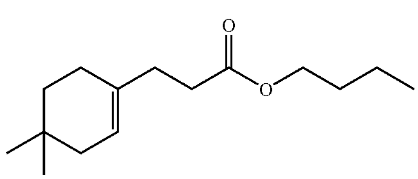 | Butyl 3-(4,4-Dimethyl-1-cyclohexen-1-yl) propanoate |
| 20 | 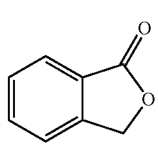 | 3H-Benzo[c]furan-1-one |

TABLE 3-continued

Structure and name of substrates used

| Substrate | Structure | Name |
|---|---|---|
| 21 | 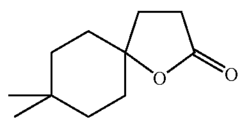 | 8,8-Dimethyl-1-oxaspiro[4.5]decan-2-one |
| 22 | 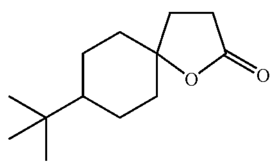 | 8-tert-Butyl-1-oxa-spiro[4.5]decan-2-one |
| 23 | 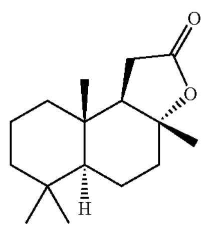 | 8,12-Epoxy-13,14,15,16-tetranorlabdan-12-one (Sclareolide) |
| 24 | 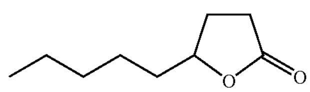 | 5-Pentyl-dihydro-furan-2-one |
| 25 | 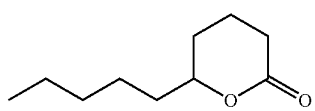 | 6-Pentyl-tetrahydro-pyran-2-one |

TABLE 4

Results obtained using the general conditions described above

| Test | Substrate (Table 3) | Conversion (%) | Isolated yield (%) |
|---|---|---|---|
| 1 | 1 | 98 | 81 |
| 2 | 2 | 98 | 85 |
| 3 | 3 | 97 | 79 |
| 4 | 4 | 98 | 78 |
| 5 | 5 | 97 | 93 |
| 6 | 6 | 94 | 75 |
| 7 | 7 | 93 | 77[1] |
| 8 | 8 | 88 | 67 |
| 9 | 9 | 72 | 46 |
| 10 | 10 | 99 | 92 |
| 11 | 11 | 98 | 82 |
| 12 | 12 | 56 | 37 |
| 13 | 13 | 94 | 82 |
| 14 | 14 | 86 | 75 |
| 15 | 15 | 56 | 45[2] |
| 16 | 16 | 97 | 82[3] |
| 17 | 17 | 94 | 72 |
| 18 | 18 | 71 | 59[4] |
| 19 | 19 | 81 | 80[1] |
| 20 | 19 | 93 | 90[2] |
| 21 | 20 | 97 | 76 |
| 22 | 21 | 79 | 56[4] |
| 23 | 22 | 75 | 68[4] |
| 24 | 23 | 97 | 91[5] |
| 25 | 24 | 98 | 91[6] |
| 26 | 25 | 98 | 93[6] |

Conversion: (in %, analysed by GC after silylation) of ester to alcohol after 2 h 30 min.
Reaction conditions: Substrate (20 mmol), $H_2$ gas (50 bars), $RuCl_2(L-1)_2$ 0.05 mol %, NaOMe 10 mol %, THF (14 mL) at 100° C. during 2 h 30 min.
[1] Reaction run for 4 h.
[2] Reaction run with KOMe (10 mol %) in THF during 5 h at 100° C. with $H_2$ gas (30 bars).
[3] Reaction run for 6 h.
[4] Reaction run with S/C = 1000 and S/B = 1 during 1 h at 100° C. with $H_2$ gas (50 bars).
[5] Reaction run with KOMe (10 mol %) in toluene during 6 h at 100° C. with $H_2$ gas (30 bars).
[6] Reaction run with KOMe (10 mol %) in toluene during 4 h at 100° C. with $H_2$ gas (50 bars).

What is claimed is:

1. A ligand of formula

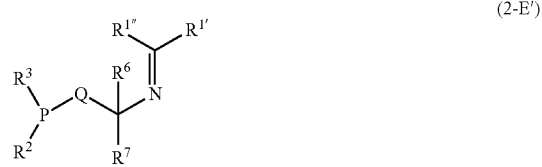

(2-E′)

wherein:
R$^{1'}$ and R$^{1'''}$ independently represent a hydrogen atom, a linear, branched or cyclic C$_1$ to C$_{10}$ alkyl or alkenyl group optionally substituted, wherein R$^{1'}$ and R$^{1'''}$, when taken separately, represent a hydrogen atom, a linear, branched or cyclic C$_1$ to C$_9$ alkyl or alkenyl group optionally substituted or a C$_6$ to C$_{10}$ aromatic group optionally substituted; or when taken together, form a saturated or unsaturated ring optionally substituted, having 5 to 12 atoms and including the carbon atom to which the R$^{1'}$ and R$^{1'''}$ groups are bonded;

R$^2$ and R$^3$ represent, simultaneously or independently, a linear, branched or cyclic C$_1$ to C$_6$ alkyl group optionally substituted, a phenyl or naphthyl group optionally substituted; or the groups R$^2$ and R$^3$, taken together, form a saturated or unsaturated ring optionally substituted, having 5, 6 or 7 atoms and including the phosphorus atom to which the R$^2$ and R$^3$ groups are bonded;

R$^6$ and R$^7$ represent, simultaneously or independently, a hydrogen atom, a linear or branched C$_1$ to C$_4$ alkyl group optionally substituted, a phenyl ring optionally substituted; R$^6$ and R$^1$, taken together, may form a saturated or unsaturated heterocycle, optionally substituted and optionally containing one additional nitrogen or oxygen atoms, containing 5 or 6 atoms and including the carbon atoms and the N atom to which the R$^6$ or R$^1$ group are bonded respectively; and Q represents:

a group of formula

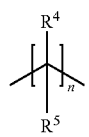

(iii)

wherein n is an integer from 2 or 3, and
R$^4$ and R$^5$ represent, simultaneously or independently, a hydrogen atom, a linear or branched C$_1$ to C$_4$ alkyl group optionally substituted, a phenyl ring optionally substituted;

or two distinct R$^4$ and/or R$^5$ groups, taken together, form a C$_5$ to C$_{10}$ saturated ring optionally substituted including the carbon atoms to which each of the R$^4$ or R$^5$ group is bonded; or a group of formula

(iv)

wherein n is an integer from 1 to 3, and
two distinct adjacent R$^4$ groups, taken together, form a C$_5$ to C$_{10}$ aromatic ring optionally substituted or a C$_5$-C$_{12}$ ferrocenediyl optionally substituted, including the carbon atoms to which each of the R$^4$ group are bonded; or three distinct adjacent R$^4$ groups, taken together, form a naphthalene ring optionally substituted, including the carbon atoms to which each of the R$^4$ group are bonded.

2. A ligand of formula

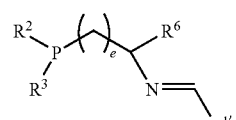

(2-F')

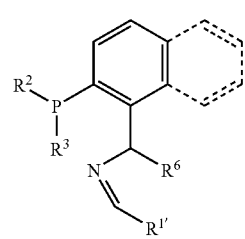

(2-G')

wherein:
the dotted lines in formula (2-G') indicate the presence of a phenyl or a naphthyl group; e represents 1 or 2;
each R$^{1'}$ represents, simultaneously or independently, a hydrogen atom, a linear, branched or cyclic C$_1$ to C$_6$ alkyl or alkenyl group optionally substituted;
R$^2$ and R$^3$, represent, simultaneously or independently, a linear, branched or cyclic C$_1$ to C$_6$ alkyl group optionally substituted, a phenyl or naphthyl group optionally substituted; or the groups R$^2$ and R$^3$, taken together, form a saturated or unsaturated ring optionally substituted, having 5, 6 or 7 atoms and including the phosphorus atom to which the R$^2$ and R$^3$ groups are bonded; and
R$^6$ represents a hydrogen atom, a linear or branched C$_1$ to C$_4$ alkyl group optionally substituted, or a phenyl group optionally substituted; or R$^6$, when taken together with R$^1$, forms a C$_3$-C$_9$ C=N function-containing heterocycle optionally substituted and optionally containing one additional nitrogen or oxygen atom, provided that 2-(diphenylphosphino)-N-(phenylmethylene)-cyclohexanamine is excluded.

3. A complex of formula

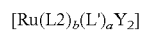

(1)

wherein:
L' represents a C$_3$-C$_{70}$ mono-phosphine or a molecule of solvent;
b is 1 and a is 1 or 2 or b is 2 and a is 0; and
each Y represents, simultaneously or independently, CO, a hydrogen or halogen atom, a hydroxyl group, a BH$_4$ or ALH$_4$ group or a C$_1$-C$_6$ alkoxy or carboxylic radical;
wherein L2 is a ligand of formula (2-E')

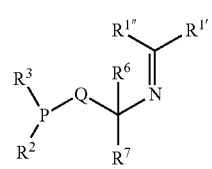

(2-E')

wherein:
R$^{1'}$ and R$^{1'''}$ independently represent a hydrogen atom, a linear, branched or cyclic C$_1$ to C$_{10}$ alkyl or alkenyl group optionally substituted, wherein R$^{1'}$ and R$^{1'''}$, when taken separately, represent a hydrogen atom, a linear, branched or cyclic C$_1$ to C$_9$ alkyl pr alkenyl group optionally substituted or a $C_6$ to $C_{10}$ aromatic group optionally substituted; or when taken together, form a saturated or unsaturated ring optionally substituted, having 5 to 12 atoms and including the carbon atom to which the $R^{1'}$ and $R^{1''}$ groups are bonded;

$R^2$ and $R^3$, when taken separately, represent, simultaneously or independently, a linear, branched or cyclic $C_1$ to $C_8$ alkyl or alkenyl group optionally substituted, a $C_6$ to $C_{10}$ aromatic group optionally substituted, or an $OR^{2'}$ or $NR^{2'}R^{3'}$ group, $R^{2'}$ and $R^{3'}$ being a $C_1$ to $C_8$ alkyl or alkenyl group; or the groups $R^2$ and $R^3$, when taken together, form a saturated or unsaturated ring optionally substituted, having 5 to 10 atoms and including the phosphorus atom to which the $R^2$ and $R^3$ groups are bonded;

$R^6$ and $R^7$ represent, simultaneously or independently, a hydrogen atom, a linear, branched or cyclic $C_1$ to $C_{10}$ alkyl or alkenyl group optionally substituted, a $C_6$-$C_{10}$ aromatic group optionally substituted, or an $OR^{4'}$ or $NR^{4'}R^{5'}$ group, $R^{4'}$ and $R^{5'}$ being a linear, branched or cyclic $C_1$ to $C_{10}$ alkyl or alkenyl group; $R^6$ and $R^1$ or $R^6$ and $R^{1''}$, taken together, may form a saturated or unsaturated heterocycle, optionally substituted and optionally containing one or two additional nitrogen or oxygen atoms, containing 5 to 10 atoms and including the carbon atoms and the N atom to which the $R^6$ or $R^1$, or $R^{1''}$, group are bonded respectively, provided that dichloro [[N(Z),1R,2R]-2-(diphenylphosphino-κP)-N-(phenylmethylene)cyclohexanamine-κN](triphenylphosphine)-Ruthenium is excluded.

4. A process for the reduction by hydrogenation of a substrate containing one or two ester or lactone functional groups into its corresponding alcohol or diol, the process comprising reducing said substrate with molecular hydrogen in the presence of a base and at least one complex in the form of a ruthenium complex of formula $$[Ru(L2)_b(L')_aY_2] \quad (1)$$

wherein L2 is a ligand of formula

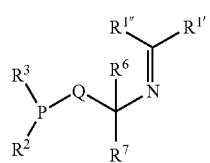

(2-E')

wherein:

$R^{1'}$ and $R^{1''}$ independently represent a hydrogen atom, a linear, branched or cyclic $C_1$ to $C_{10}$ alkyl or alkenyl group optionally substituted, wherein $R^{1'}$ and $R^{1''}$, when taken separately, represent a hydrogen atom, a linear, branched or cyclic $C_1$ to $C_9$ alkyl or alkenyl group optionally substituted or a $C_6$ to $C_{10}$ aromatic group optionally substituted; or when taken together, form a saturated or unsaturated ring optionally substituted, having 5 to 12 atoms and including the carbon atom to which the $R^{1'}$ and $R^{1''}$ groups are bonded;

$R^2$ and $R^3$, when taken separately, represent, simultaneously or independently, a linear, branched or cyclic $C_1$ to $C_8$ alkyl or alkenyl group optionally substituted, a $C_6$ to $C_{10}$ aromatic group optionally substituted, or an $OR^{2'}$ or $NR^{2'}R^{3'}$ group, $R^{2'}$ and $R^{3'}$ being a $C_1$ to $C_8$ alkyl or alkenyl group; or the groups $R^2$ and $R^3$, when taken together, form a saturated or unsaturated ring optionally substituted, having 5 to 10 atoms and including the phosphorus atom to which the $R^2$ and $R^3$ groups are bonded;

$R^6$ and $R^7$ represent, simultaneously or independently, a hydrogen atom, a linear, branched or cyclic $C_1$ to $C_{10}$ alkyl or alkenyl group optionally substituted, a $C_6$-$C_{10}$ aromatic group optionally substituted, or an $OR^{4'}$ or $NR^{4'}R^{5'}$ group, $R^{4'}$ and $R^{5'}$ being a linear, branched or cyclic $C_1$ to $C_{10}$ alkyl or alkenyl group; $R^6$ and $R^1$ or $R^6$ and $R^{1''}$, taken together, may form a saturated or unsaturated heterocycle, optionally substituted and optionally containing one or two additional nitrogen or oxygen atoms, containing 5 to 10 atoms and including the carbon atoms and the N atom to which the $R^6$ or $R^1$, or $R^{1''}$, group are bonded respectively; and Q represents:

a group of formula

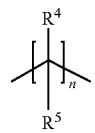

(i)

wherein n is an integer from 1 to 4, and $R^4$ and $R^5$ represent, simultaneously or independently, a hydrogen atom, a linear, branched or cyclic $C_1$ to $C_{10}$ alkyl alkenyl group optionally substituted, a $C_6$-$C_{10}$ aromatic group optionally substituted, or an $OR^{4'}$ or $NR^{4'}R^{5'}$ group, $R^{4'}$ and $R^{5'}$ being a linear, branched or cyclic $C_1$ to $C_{10}$ alkyl or alkenyl group; two distinct $R^4$ and/or $R^5$ groups, taken together, may form a $C_5$ to $C_{10}$, saturated ring optionally substituted, including the carbon atoms to which each of the $R^4$ or $R^5$ group is bonded; or a group of formula

(ii)

wherein n is an integer from 2 to 4, and two distinct adjacent $R^4$ groups, taken together, form a $C_5$ to $C_{10}$, aromatic ring optionally substituted or a $C_5$-$C_{12}$ metallocenediyl optionally substituted, including the carbon atoms to which each of the $R^4$ group are bonded; or three distinct adjacent $R^4$ groups, taken together, form a naphthalene ring optionally substituted, including the carbon atoms to which each of the $R^4$ groups are bonded;

and wherein the substituents of and $R^{1'}$, $R^{1''}$ and $R^1$ to $R^7$ and Q are one or two halogen, $C_1$ to $C_{10}$ alkoxy or polyalkyleneglycols groups, halo- or perhalo-hydrocarbon, COOR, $NR_2$, quaternary amine or R groups, wherein R is a $C_1$ to $C_6$ alkyl, or a $C_5$ to $C_{12}$ cycloalkyl, aralkyl or aromatic group, the latter being also optionally substituted by one, two or three halogen, sulfonates groups or $C_1$-$C_8$ alkyl, alkoxy, amino, nitro, sulfonates, halo- or perhalo-hydrocarbon or ester groups;

L' represents a $C_3$-$C_{70}$ mono-phosphine or a molecule of solvent;

b is 1 and a is 1 or 2 or b is 2 and a is 0; and each Y represents, simultaneously or independently, CO, a hydrogen or halogen atom, a hydroxyl group, a $BH_4$ or $ALH_4$ group or a $C_1$-$C_6$ alkoxy or carboxylic radical. and wherein the substrate is a compound of formula (I)

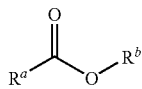
(I)

wherein $R^a$ and $R^b$ represent, simultaneously or independently, a linear, branched or cyclic $C_1$-$C_{30}$ aromatic, alkyl or alkenyl group optionally substituted; or $R^a$ and $R^b$ are bonded together and form a $C_4$-$C_{20}$ saturated or unsaturated group, optionally substituted; and wherein the substituents of $R^a$ and $R^b$ are a $COOR^c$, group, one, two or three halogen, $OR^c$, $NR^c_2$ or $R^c$ groups, in which $R^c$ is a hydrogen atom, a halogenated $C_1$-$C_2$ group or a $C_1$ to $C_{10}$ cyclic, linear or branched alkyl, or alkenyl group.

5. The process according to claim 4, wherein the ruthenium complex is of formula $$[Ru(L2)_2Y_2] \quad (2)$$

wherein L2 and Y have the meaning indicated in claim 4.

6. The process according to claim 4, wherein the base has a $pK_a$ above 14.

7. The process according to claim 4, wherein the base is an alkaline or alkaline-earth metal carbonates, an alkaline or alkaline-earth metal hydroxides, $C_{1-10}$ amidures, $C_{10-26}$ phosphazine or an alcoholate of formula $(R^{13}O)_2M$ or $R^{13}OM'$, wherein M is an alkaline-earth metal, M' is an alkaline metal or an ammonium $NR^{14}_4{}^+$, $R^{13}$ stands for hydrogen or a $C_1$ to $C_6$ linear or branched alkyl radical and $R^{14}$ stands for a $C_1$ to $C_{10}$ linear or branched alkyl radical.

8. A process for the reduction by hydrogenation of a substrate containing one or two ester or lactone functional groups into its corresponding alcohol or diol, the process comprising reducing said substrate with molecular hydrogen in the presence of a base and at least one complex in the form of a ruthenium complex of formula $$[Ru(L2)_b(L')_aY_2] \quad (1)$$

wherein L2 is a ligand as defined in claim 1,

L' represents a $C_3$-$C_{70}$ mono-phosphine or a molecule of solvent;

b is 1 and a is 1 or 2 or b is 2 and a is 0; and each Y represents, simultaneously or independently, CO, a hydrogen or halogen atom, a hydroxyl group, a $BH_4$ or $ALH_4$ group or a $C_1$-$C_6$ alkoxy or carboxylic radical. and wherein the substrate is a compound of formula (I)

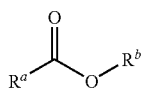
(I)

wherein $R^a$ and $R^b$ represent, simultaneously or independently, a linear, branched or cyclic $C_1$-$C_{30}$ aromatic, alkyl or alkenyl group optionally substituted; or $R^a$ and $R^b$ are bonded together and form a $C_4$-$C_{20}$ saturated or unsaturated group, optionally substituted; and wherein the substituents of $R^a$ and $R^b$ are a $COOR^c$, group, one, two or three halogen, $OR^c$, $NR^c_2$ or $R^c$ groups, in which $R^c$ is a hydrogen atom, a halogenated $C_1$-$C_2$ group or a $C_1$ to $C_{10}$ cyclic, linear or branched alkyl, or alkenyl group.

9. The process according to claim 8, wherein the ruthenium complex is of formula $$[Ru(L2)_2Y_2] \quad (2)$$

wherein L2 and Y have the meaning indicated in claim 8.

10. The process according to claim 8, wherein the base has a $pK_a$ above 14.

11. The process according to claim 8, wherein the base is an alkaline or alkaline-earth metal carbonates, an alkaline or alkaline-earth metal hydroxides, $C_{1-10}$ amidures, $C_{10-26}$ phosphazine or an alcoholate of formula $(R^{13}O)_2M$ or $R^{13}OM'$, wherein M is an alkaline-earth metal, M' is an alkaline metal or an ammonium $NR^{14}_4{}^+$, $R^{13}$ stands for hydrogen or a $C_1$ to $C_6$ linear or branched alkyl radical and $R^{14}$ stands for a $C_1$ to $C_{10}$ linear or branched alkyl radical.

12. A process for the reduction by hydrogenation of a substrate containing one or two ester or lactone functional groups into its corresponding alcohol or diol, the process comprising reducing said substrate with molecular $H_2$-in the presence of a base and at least one complex in the form of a ruthenium complex of formula $$[Ru(L2)_b(L')_aY_2] \quad (1)$$

wherein L2 is a ligand as defined in claim 2,

L' represents a $C_3$-$C_{70}$ mono-phosphine or a molecule of solvent;

b is 1 and a is 1 or 2 or b is 2 and a is 0; and each Y represents, simultaneously or independently, CO, a hydrogen or halogen atom, a hydroxyl group, a $BH_4$ or $ALH_4$ group or a $C_1$-$C_6$ alkoxy or carboxylic radical. and wherein the substrate is a compound of formula (I)

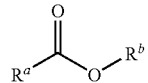
(I)

wherein $R^a$ and $R^b$ represent, simultaneously or independently, a linear, branched or cyclic $C_1$-$C_{30}$ aromatic, alkyl or alkenyl group optionally substituted; or $R^a$ and $R^b$ are bonded together and form a $C_4$-$C_{20}$ saturated or unsaturated group, optionally substituted; and wherein the substituents of $R^a$ and $R^b$ are a $COOR^c$, group, one, two or three halogen, $OR^c$, $NR^c_2$ or $R^c$ groups, in which $R^c$ is a hydrogen atom, a halogenated $C_1$-$C_2$ group or a $C_1$ to $C_{10}$ cyclic, linear or branched alkyl, or alkenyl group.

13. The process according to claim 12, wherein the ruthenium complex is of formula $$[Ru(L2)_2Y_2] \quad (2)$$

wherein L2 and Y have the meaning indicated in claim 12.

14. The process according to claim 12, wherein the base has a $pK_a$ above 14.

15. The process according to claim 12, wherein the base is an alkaline or alkaline-earth metal carbonates, an alkaline or alkaline-earth metal hydroxides, $C_{1-10}$ amidures, $C_{10-26}$ phosphazine or an alcoholate of formula $(R^{13}O)_2M$ or $R^{13}OM'$, wherein M is an alkaline-earth metal, M' is an alkaline metal or an ammonium $NR^{14}_4{}^+$, $R^{13}$ stands for hydrogen or a $C_1$ to $C_6$ linear or branched alkyl radical and $R^{14}$ stands for a $C_1$ to $C_{10}$ linear or branched alkyl radical.

16. A complex of formula $$[Ru(L2)_b(L')_a Y_2] \qquad (1)$$

wherein

L' represents a $C_3$-$C_{70}$ mono-phosphine or a molecule of solvent;

b is 1 and a is 1 or 2 or b is 2 and a is 0; and each Y represents, simultaneously or independently, CO, a hydrogen or halogen atom, a hydroxyl group, a $BH_4$ or $ALH_4$ group or a $C_1$-$C_6$ alkoxy or carboxylic radical;

wherein L2 is a ligand of formula (2-F') as defined in claim 1, provided that dichloro[[N(Z),1R]-2R]-2-(diphenylphosphino-κP)-N-(phenylmethylene)cyclohexanamine-κN] (triphenylphosphine)-Ruthenium is excluded.

17. A complex of formula $$[Ru(L2)_b(L')_a Y_2] \qquad (1)$$

wherein

L' represents a $C_3$-$C_{70}$ mono-phosphine or a molecule of solvent;

b is 1 and a is 1 or 2 or b is 2 and a is 0; and each Y represents, simultaneously or independently, CO, a hydrogen or halogen atom, a hydroxyl group, a $BH_4$ or $ALH_4$ group or a $C_1$-$C_6$ alkoxy or carboxylic radical;

wherein L2 is a ligand of formula (2-G') as defined in claim 2, provided that dichloro[[N(Z),1R,2R]-2-(diphenylphosphino-κP)-N-(phenylmethylene)cyclohexanamine-κN] triphenylphosphine)-Ruthenium is excluded.

18. A process for the reduction by hydrogenation of a substrate containing one or two ester or lactone functional groups into its corresponding alcohol or diol, the process comprising reducing said substrate with molecular hydrogen in the presence of a base and at least one ruthenium complex according to claim 3;

wherein the substrate is a compound of formula (I)

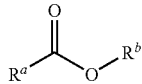
(I)

wherein $R^a$ and $R^b$ represent, simultaneously or independently, a linear, branched or cyclic $C_1$-$C_{30}$ aromatic, alkyl or alkenyl group optionally substituted; or $R^a$ and $R^b$ are bonded together and form a $C_4$-$C_{20}$ saturated or unsaturated group, optionally substituted; and wherein the substituents of $R^a$ and $R^b$ are a $COOR^c$, group, one, two or three halogen, $OR^c$, $NR^c_2$ or $R^c$ groups, in which $R^c$ is a hydrogen atom, a halogenated $C_1$-$C_2$ group or a $C_1$ to $C_{10}$ cyclic, linear or branched alkyl, or alkenyl group.

19. A process for the reduction by hydrogenation of a substrate containing one or two ester or lactone functional groups into its corresponding alcohol or diol, the process comprising reducing said substrate with molecular hydrogen in the presence of a base and at least one ruthenium complex according to claim 17;

wherein the substrate is a compound of formula (I)

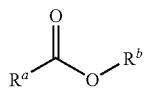
(I)

wherein $R^a$ and $R^b$ represent, simultaneously or independently, a linear, branched or cyclic $C_1$-$C_{30}$ aromatic, alkyl or alkenyl group optionally substituted; or $R^a$ and $R^b$ are bonded together and form a $C_4$-$C_{20}$ saturated or unsaturated group, optionally substituted; and wherein the substituents of $R^a$ and $R^b$ are a $COOR^c$, group, one, two or three halogen, $OR^c$, $NR^c_2$ or $R^c$ groups, in which $R^c$ is a hydrogen atom, a halogenated $C_1$-$C_2$ group or a $C_1$ to $C_{10}$ cyclic, linear or branched alkyl, or alkenyl group.

20. A process for the reduction by hydrogenation of a substrate containing one or two ester or lactone functional groups into its corresponding alcohol or diol, the process comprising reducing said substrate with molecular hydrogen in the presence of a base and at least one ruthenium complex according to claim 16;

wherein the substrate is a compound of formula (I)

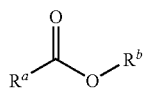
(I)

wherein $R^a$ and $R^b$ represent, simultaneously or independently, a linear, branched or cyclic $C_1$-$C_{30}$ aromatic, alkyl or alkenyl group optionally substituted; or $R^a$ and $R^b$ are bonded together and form a $C_4$-$C_{20}$ saturated or unsaturated group, optionally substituted; and wherein the substituents of $R^a$ and $R^b$ are a $COOR^c$, group, one, two or three halogen, $OR^c$, $NR^c_2$ or $R^c$ groups, in which $R^C$ is a hydrogen atom, a halogenated $C_1$-$C_2$ group or a $C_1$ to $C_{10}$ cyclic, linear or branched alkyl, or alkenyl group.

* * * * *

UNITED STATES PATENT AND TRADEMARK OFFICE
CERTIFICATE OF CORRECTION

PATENT NO. : 7,763,758 B2  Page 1 of 1
APPLICATION NO. : 11/854106
DATED : July 27, 2010
INVENTOR(S) : Saudan et al.

It is certified that error appears in the above-identified patent and that said Letters Patent is hereby corrected as shown below:

Column 28:
Line 67, before "alkenyl", change "pr" to -- or --.

Column 30:
Line 26, before "alkenyl", insert -- or --.
Line 52, before "$R^{1'}$," delete "and".

Column 31:
Line 48, change "radical. and" to -- radical; and --.

Column 32:
Line 20, change "H2-in" to -- H2 in --.

Column 33:
Line 13, change "dichloro[[N(Z),1R]-2R]-2-(diphenylphos-" to
-- dichloro[[N(Z),1R,2R]-2-(diphenylphos- --.
Line 29, change "triphenylphosphine)-Ruthenium" to -- (triphenylphosphine)-Ruthenium --.

Signed and Sealed this

Sixteenth Day of November, 2010

David J. Kappos
*Director of the United States Patent and Trademark Office*